United States Patent [19]
Hart

[11] Patent Number: 5,643,292
[45] Date of Patent: Jul. 1, 1997

[54] PERCUTANEOUS SUTURING DEVICE

[75] Inventor: Charles C. Hart, Huntington Beach, Calif.

[73] Assignee: Applied Medical Resources Corporation, Laguna Hills, Calif.

[21] Appl. No.: 370,863

[22] Filed: Jan. 10, 1995

[51] Int. Cl.$^6$ ............................................. A61B 17/00
[52] U.S. Cl. ....................... 606/144; 606/139; 606/223; 112/169
[58] Field of Search ............................ 606/139, 144, 606/145–148, 222–223; 112/169, 80.03, 222; 223/102–104; 289/16; 604/272

[56] References Cited

U.S. PATENT DOCUMENTS

| | | | |
|---|---|---|---|
| 636,728 | 11/1899 | Kindel | 223/103 |
| 1,583,271 | 5/1926 | Biro | 606/144 |
| 3,638,653 | 2/1972 | Berry . | |
| 3,638,654 | 2/1972 | Akuba . | |
| 3,877,434 | 4/1975 | Ferguson et al. | 606/148 |
| 4,235,238 | 11/1980 | Ogiu et al. . | |
| 4,244,370 | 1/1981 | Furlow et al. . | |
| 4,392,495 | 7/1983 | Bayers . | |
| 4,852,568 | 8/1989 | Kensey . | |
| 4,873,976 | 10/1989 | Schreiber . | |
| 4,935,027 | 6/1990 | Yoon | 606/148 |
| 4,944,443 | 7/1990 | Oddsen et al. . | |
| 4,957,498 | 9/1990 | Caspari | 606/146 |
| 4,981,149 | 1/1991 | Yoon et al. . | |
| 5,015,250 | 5/1991 | Foster . | |
| 5,129,912 | 7/1992 | Noda et al. . | |
| 5,174,276 | 12/1992 | Crockard | 606/142 |
| 5,203,864 | 4/1993 | Phillips . | |
| 5,234,445 | 8/1993 | Walker et al. . | |
| 5,269,809 | 12/1993 | Hayhurst et al. . | |
| 5,281,237 | 1/1994 | Gimpelson . | |
| 5,290,296 | 3/1994 | Phillips . | |
| 5,312,422 | 5/1994 | Trott . | |
| 5,312,423 | 5/1994 | Rosenbluth et al. | 606/148 |
| 5,318,578 | 6/1994 | Harrith . | |
| 5,320,629 | 6/1994 | Noda et al. . | |
| 5,324,306 | 6/1994 | Makower et al. | 606/108 |
| 5,330,491 | 7/1994 | Walker et al. . | |
| 5,346,498 | 9/1994 | Greelis et al. | 606/108 |
| 5,350,385 | 9/1994 | Christy . | |
| 5,354,298 | 10/1994 | Lee et al. . | |
| 5,356,424 | 10/1994 | Buzerak et al. . | |
| 5,358,498 | 10/1994 | Shave . | |
| 5,364,408 | 11/1994 | Gordon . | |
| 5,364,410 | 11/1994 | Failla et al. . | |
| 5,368,601 | 11/1994 | Sauer et al. . | |
| 5,387,227 | 2/1995 | Grice | 606/148 |
| 5,462,560 | 10/1995 | Stevens | 606/148 |
| 5,501,692 | 3/1996 | Riza | 606/148 |
| 5,507,758 | 4/1996 | Thomason et al. | 606/139 |

FOREIGN PATENT DOCUMENTS 969254  10/1982  U.S.S.R. ........................ 606/144

OTHER PUBLICATIONS

American Design Group, Inc., Arthroscopy Cheater Brochure, Apr. 3, 1989.

*Primary Examiner*—Jeffrey A. Schmidt
*Attorney, Agent, or Firm*—Richard L. Myers

[57] ABSTRACT

A suturing device includes a handle and an elongate needle having a hollow lumen. The needle is insertable percutaneously to form a suture around tissue portions within a body cavity. Initially the needle is inserted through the tissue portions and one end of a suture is deployable through the lumen of the needle by operation of the handle. The needle can then be retracted leaving the suture extending through the tissue portions. A snare also positioned within the lumen of the needle is deployable by operation of the handle to engage and capture the free end of the suture. Both ends of the suture can then be removed and a slip knot tied to form the suture. The snare can be formed in a hook configuration and maintained in a particular plane as it is deployed and retracted. This enables the hook to be guided back into the lumen in order to capture the free end of the suture line and facilitate retraction of the suturing device. Single-handed operation of the suturing device is emphasized in an associated method.

16 Claims, 6 Drawing Sheets

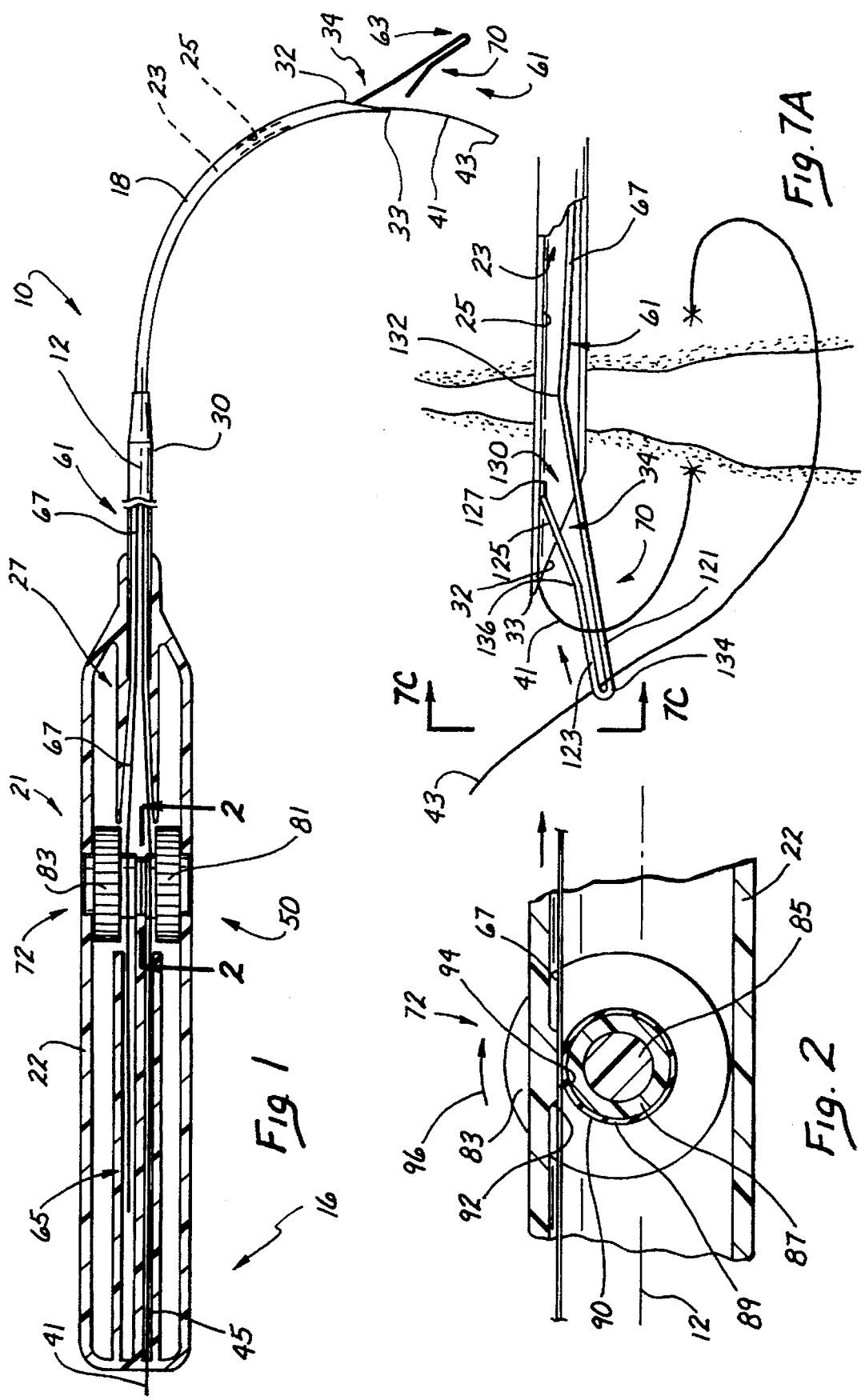

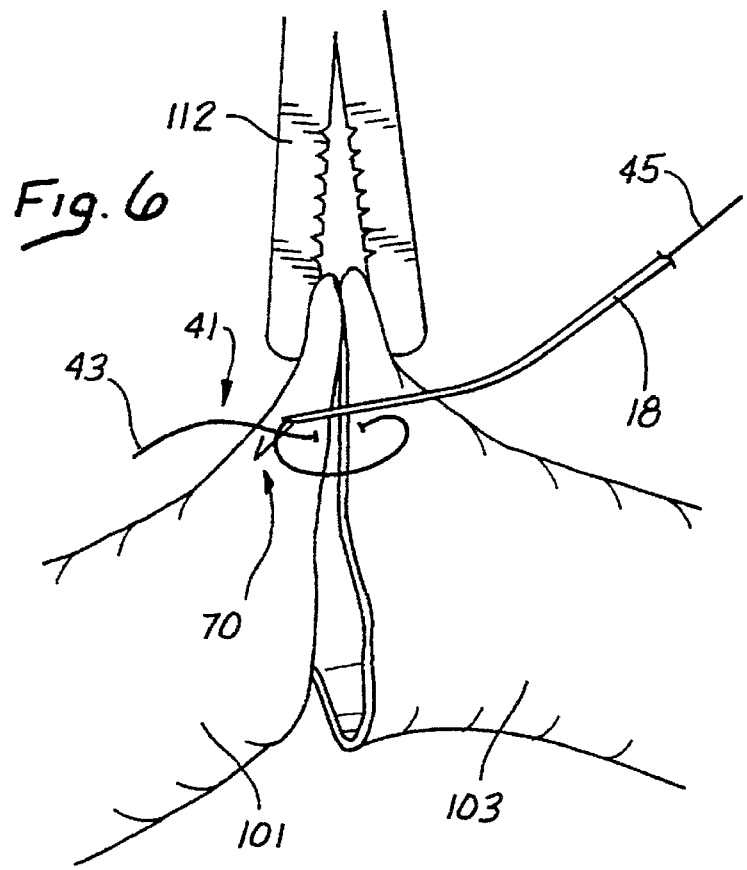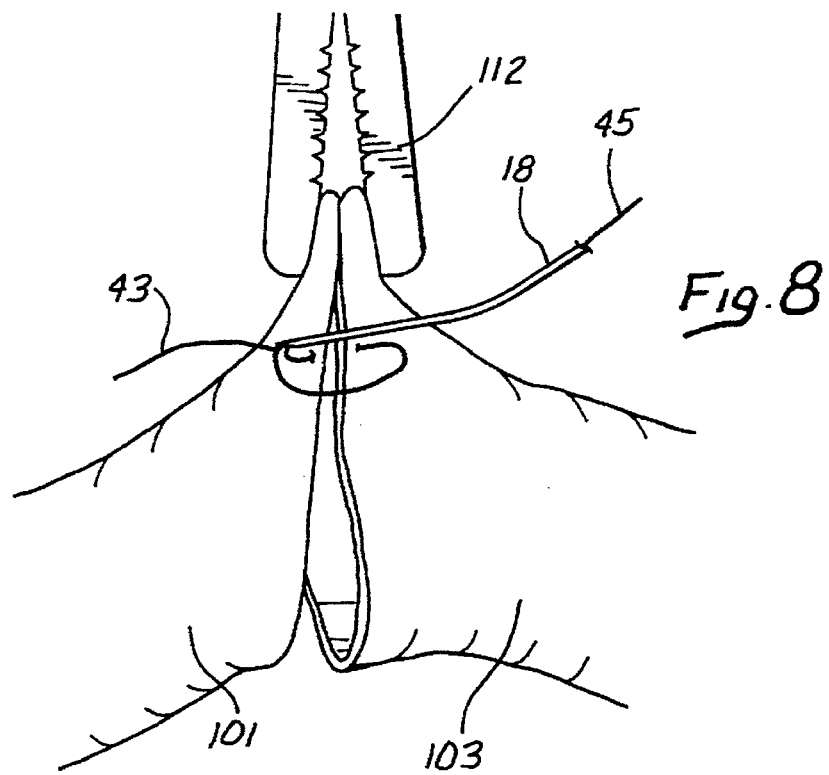

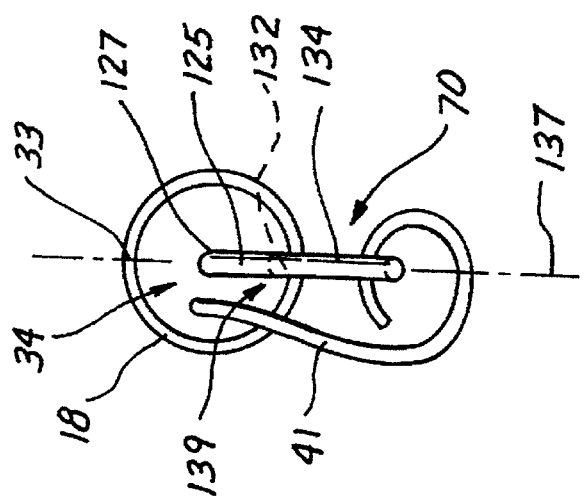
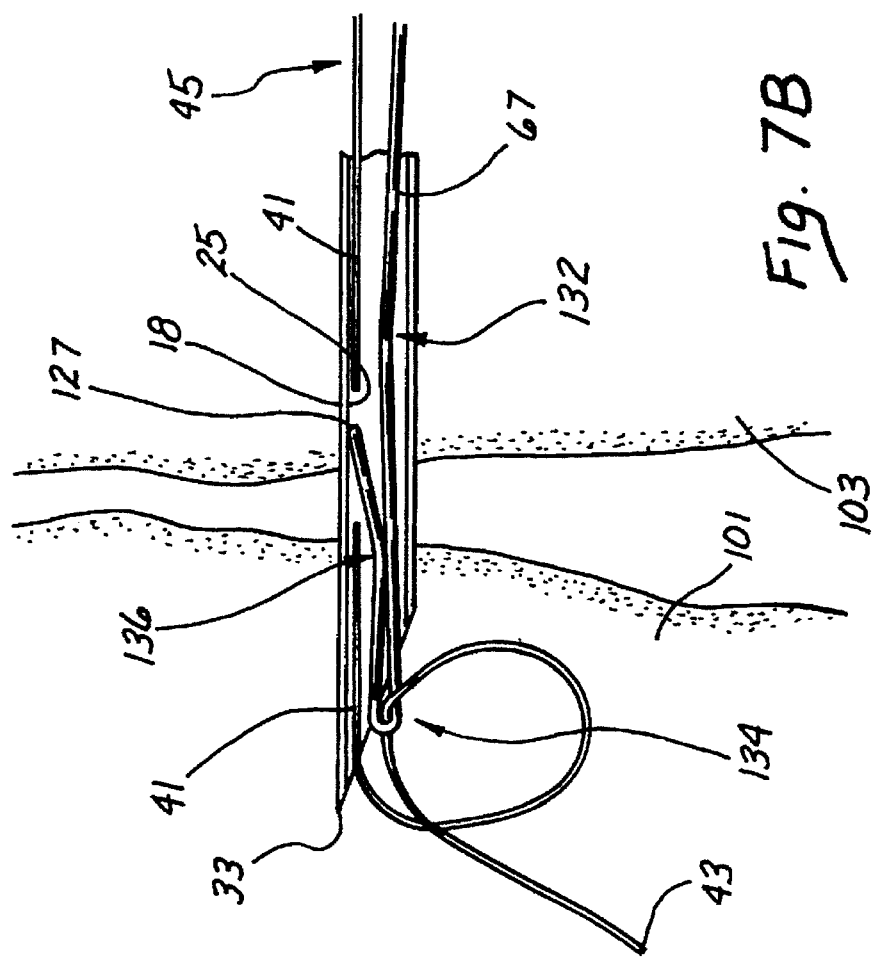

PERCUTANEOUS SUTURING DEVICE

BACKGROUND OF THE INVENTION

1. Field of the Invention

This invention relates generally to devices for suturing tissue and more specifically for such devices which are adapted for percutaneously suturing tissue within a body cavity.

2. Discussion of the Prior Art

In the past, suturing has been used to join two pieces of tissue typically in an open surgery environment. In such an environment, visualization and access to the pieces of tissue is generally of little concern. A needle with an attached suture is grasped by a scissor clamp and inserted through the tissue pieces. The clamp disengages the needle on one side of the pieces and grasps the needle on the other side of the pieces to draw the suture through the tissue. Opposing ends of the suture (line) are then joined to form the suture.

With the advent of less invasive surgeries, it has become desirable to form sutures on the interior side of a body wall, such as the abdominal wall, and within a body cavity, such as the abdominal cavity. Under these circumstances, the suture line must be inserted through the abdominal wall and the tissue pieces within the abdominal cavity. The (free) end of the suture line must then be engaged and joined to the opposing end of the suture line to form the suture around the two pieces within the body cavity. This percutaneous suturing has been preformed with a suture line apparatus which can be sharpened to form a needle which is then inserted directly through the body wall. Alternatively, the percutaneous suturing device can be adapted for insertion through a trocar providing access across the body wall. Whether inserted directly through the body wall or through a trocar, the device engages the tissue pieces interiorly of the body cavity and issues the suture line through the needle.

In the past, a separate device in the nature of a retractor has been inserted percutaneously to grasp the free end of the suture line. The opposing ends of the suture line are then joined to form the suture around the tissue pieces. In some cases, both the suture line device and the retractor have been removed through a common hole in the body wall and the suture knot has been formed exteriorly of the body wall. The knot has been then pushed through the common opening to form the suture around the tissue pieces interiorly of the body cavity.

In the case of these devices of the prior art, the formation of a single suture has been very complex involving several instruments and at least two hands. The visualization of the complex formation of the suture has been a problem requiring even further apparatus and manipulation to accommodate the procedure.

SUMMARY OF THE INVENTION

In accordance with the present invention, a single suturing device is provided and adapted to be held in a single hand of the user. The device includes a tube having a longitudinal channel and a needle disposed at its distal end. A suture line is disposed in the tubular channel along with a snare. In operation, the needle of the device is inserted percutaneously, either through the body wall, or through a trocar and passed through the tissue pieces to be joined. A thumb wheel operated by the single hand of the user issues the free end of the suture line to exit the needle through the tissue pieces.

A second thumb wheel forming part of the housing of the device, is then operable by the single hand of the user to deploy the snare from the common channel of the tube. The snare has a unique hook configuration for initially engaging the free end of the suture line, for gripping the suture line, and for drawing the free end of the suture line toward the tube of the device. Removal of the device from the tissue pieces automatically passes additional suture line between the two pieces. A suturing knot can be formed interiorly of the body cavity, or alternatively, the device can be removed from the body cavity and the opposing ends of the suture line joined to form the suture knot. This knot can then be slipped back through the opening in the body wall to form a tight suture around the tissue pieces.

In one aspect, the invention includes a suturing device for suturing tissue within a body cavity defined by a body wall. An elongate needle having an axis and a lumen extending along the axis between a proximal end and a distal end is coupled to a handle at a proximal end of the needle. The handle forms an enclosure defining a chamber communicating with the lumen of the needle and is sized and configured to be held in the single hand of the user. A suture line includes a first end which is positionable in the lumen of the needle and a second end positionable in the chamber of the enclosure. First means included in the handle is operable by the single hand of the user to issue the first end of the suture line from the needle. A snare disposed in the lumen of the needle has a first position proximal to the needle and a second position spaced from the needle. The device includes second means included in the handle and operable by the single hand of the user for deploying the snare from the first position to the second position to capture the first end of the suture line, and for retracting the snare and the captured first end of the suture line from the second position to the first position. The snare includes a hook having an open state and a closed state, means is included in the handle for moving the hook to the open state to engage the suture line and to the closed state to capture the suture line.

An additional aspect of the invention includes a method for suturing tissue within a body cavity defined by a body wall. This method includes the steps of providing a device including an elongate needle having a proximal end and a distal end and a handle disposed at the proximal end of the needle which is adapted to be held in the single hand of the user. Positioning a suture line within the handle enables the needle to be inserted through the body wall and through the tissue pieces in the body cavity by operating the handle with the single hand of the user. Issuing the suture line through the needle by operation of the handle using the single hand of the user positions the distal end of the suture line on one side of the tissue pieces and the proximal end of the suture line on the other side of the tissue pieces. Capturing the distal end of the suture line by operation of the handle using the single hand of the user facilitates tying a knot between the distal end and the proximal end of the suture line to form the suture around the tissue pieces.

In a particular method, the capturing step includes the step of operating the handle to deploy a snare from the distal end of the needle, the snare having an open state and a closed state. Operating the handle to move the snare to the open state permits the suture line to be engaged. Operating the handle to move the snare to the closed state permits the suture line to be captured by the snare.

Thus, a suture can be formed within a body cavity using a single device which can be manipulated using a single hand. Both the introduction of the suture line through the tissue pieces and the retraction of opposing ends of the suture line can be accomplished with the same device. The opposite hand of the surgeon can be involved with other surgical procedures such as manipulation of a grasper for holding tissue or scope or other apparatus for visualizing the procedure.

These and other features and advantages of the invention will become more apparent with a discussion of preferred embodiments and method steps, and reference to the associated drawings.

DESCRIPTION OF THE DRAWINGS

FIG. 1 is a top plan view, partially in axial cross section of one embodiment of the suturing device of the present invention;

FIG. 2 is a cross section view of a thumb wheel taken along lines 2—2 of FIG. 1;

FIG. 3–FIG. 10 illustrate steps in a preferred method for suturing within a body cavity in accordance with a method associated with the present invention;

FIG. 3 is a perspective view of a clamp holding two pieces of tissue and the needle of a suturing device extending through the two tissue pieces;

FIG. 4 is a perspective view illustrating a snare deployed from the needle to permit a distal end of the suture line to be issued from the needle;

FIG. 5 is a perspective view illustrating the snare retracted into the needle with the distal end of the suture line extending from the needle and between the two tissue pieces;

FIG. 6 is a perspective view illustrating the needle withdrawn from the two tissue pieces, the snare deployed from the needle in an open state to engage the distal end of the suture line;

FIG. 7A is an enlarged perspective view illustrating the snare in engaging relationship with the distal end of the suture line and being withdrawn toward the needle;

FIG. 7B is a perspective view similar to FIG. 7A and illustrating the snare withdrawn further into sliding engagement with the interior surface of the needle to pinch the distal end of the suture line and capture the suture line in the snare;

FIG. 7C is an end elevation view taken along lines 7C—7C of FIG. 7A;

FIG. 8 is a perspective view illustrating both the distal and the proximal ends of the suture line disposed in the needle of the device;

FIG. 9 is a perspective view illustrating the device being removed from the tissue pieces as additional suture line is drawn through the tissue pieces; and FIG. 10 is a perspective view illustrating a knot tied between the distal and proximal ends of the suture line and slipped into engagement with the tissue pieces to form the suture.

DESCRIPTION OF PREFERRED EMBODIMENTS AND BEST MODE OF THE INVENTION

Figure 3:
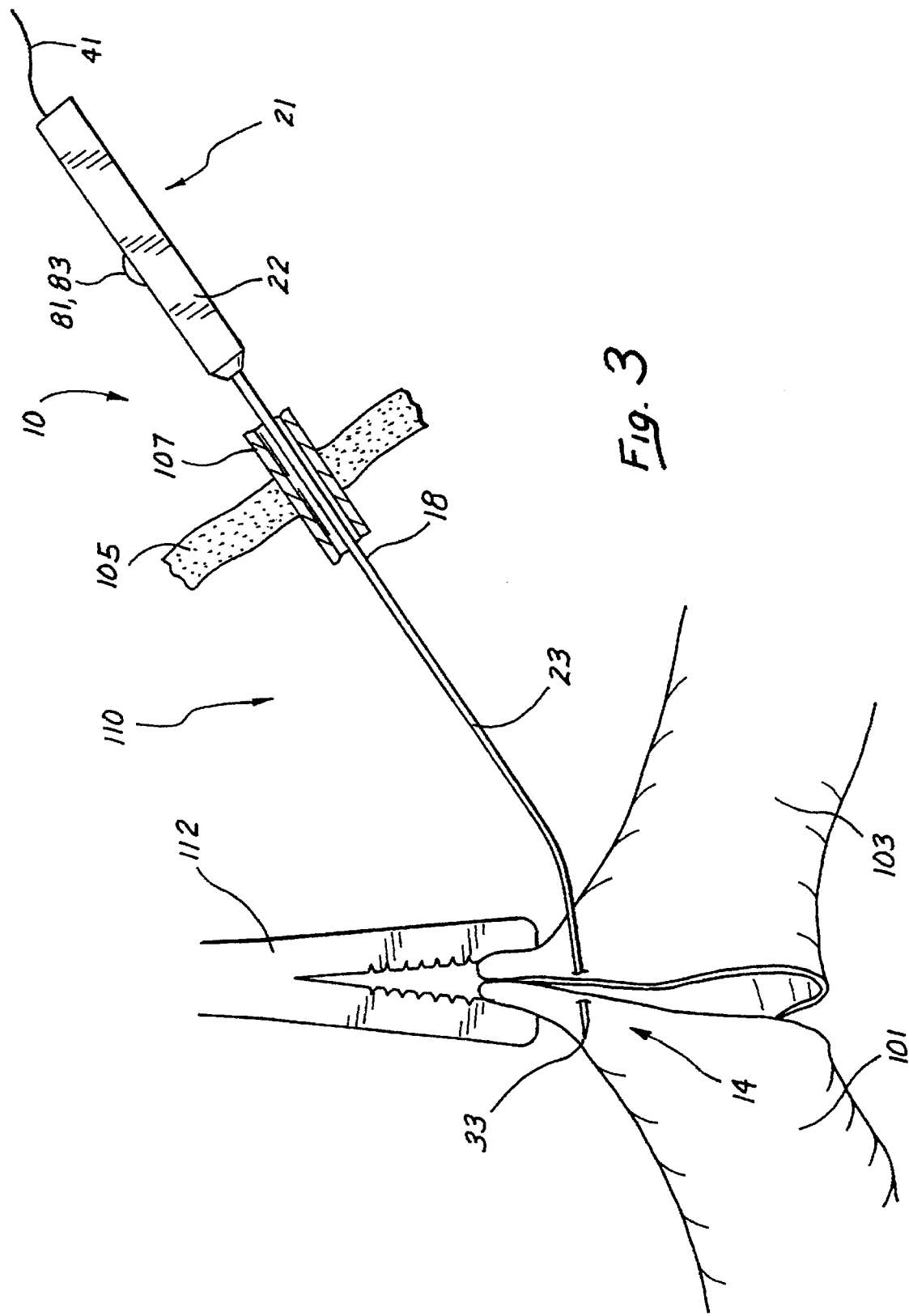

A suturing device is illustrated in FIG. 1 and designated generally by the reference numeral 10. The device 10 has an elongate configuration with an axis 12 extending generally between a distal end 14 and a proximal end 16. An elongate tube typically having the configuration of a needle 18 is disposed at the distal end 14 of the device 10 and coupled to a handle 21 at the proximal end 16 of the device 10. The needle 18 includes at least one lumen 23 which is defined by an inner surface 25 and extends along the axis 12.

The handle 21 includes a housing 22 that defines a chamber 27 which communicates with the lumen 23 of the needle 18. In a preferred embodiment, the housing 22 is molded from a plastic material such as polycarbonate, and the tube or needle 18 is formed from surgical stainless steel. Stress relief is provided by a tubular member 30 at the junction of the needle 18 and housing 22.

The distal end of the needle 18 can be sharpened along a bevel 32 not only to form a point 33 on the needle 18, but also to form a lateral opening 34 which exposes at least a portion of the inner surface 25.

Of particular interest to the present invention is a suture line 41 having a free end 43 at the distal end 14 of the device 10, and a proximal end 45 at the proximal end 16 of the device 10. In a particular embodiment, the proximal end 45 of the suture line 41 may extend entirely through the handle 41 as illustrated in FIG. 1, or may be wound on a bobbin (not shown) within the handle 21. In either case, the proximal end 16 is intended to provide a generally unlimited supply of the suture line 41. The handle 21 includes a mechanism 50 described in greater detail below, which is operable to issue the distal end 43 of the suture line 41 through the lumen 23 and at the distal end 14 of the device 10.

Also of particular interest to the present invention is a snare 61 having a distal end 63 and proximal end 65. A wire 67 of the snare 61 is disposed at the proximal end and extends from the chamber 27 of the housing 22 and through the lumen 23 of the needle 18. At the distal end 63, the wire 67 is bent back on itself to form a hook 70 which is described in greater detail below.

A mechanism 72 is included in the handle 21 provides means for deploying at least the hook 70 of the snare 61 from the distal end 14 of the needle 18, and for retracting at least the hook of the snare 61 into the lumen 23.

The mechanism 50 for issuing the suture line 41 and the mechanism 72 for deploying and retracting the snare 61, form mirror images of each other in a preferred embodiment. The mechanism 72 is illustrated in the axial cross section view of FIG. 2.

Both of the mechanisms 50 and 72 form part of the handle 21 and include thumb wheels 81 and 83 respectively, that are pivotal on a common stationary shaft 85 which extends transverse to the axis 12. As further illustrated in FIG. 2, the thumbwheel 83 of the mechanism 72 has a fixed relationship with an annular flange 87 which pivots on the shaft 85. A rubberized coating or sleeve 89 is provided on the outer surface of the flange 87 to form a surface 90 having a high coefficient of friction.

This surface 90 rotates in close proximity to a flange 92 which forms part of the housing 22 and extends to an inner surface 94. In the illustrated embodiment, the wire 67 of the snare 61 is directed between the stationary surface 94, which has a low coefficient of friction, and the annular surface 90, which has a high coefficient of friction. Accordingly, when the surface 90 moves in close proximity to the surface 94 with the wire 67 disposed therebetween, the wire 67 moves with the rubber sleeve 89 relative to the flange 92. It follows that when the thumb wheel 83 is rotated clockwise in FIG. 2, as illustrated by an arrow 96, the snare 61 is deployed from the distal end 14 of the suturing device 10. Conversely, when the thumb handle 83 is rotated counter-clockwise in FIG. 2, the snare 61 is retracted toward the lateral opening 34 in the needle 18.

The processes for issuing the suture 41 by operation of the thumb wheel 81, and for deploying and retracting the snare 61 by operation of the thumb wheel 83 will be better understood with reference to the method steps illustrated in FIGS. 3 through 10.

The surgical operation contemplated in FIG. 3 requires the joining of two pieces of tissue 101 and 103, each having a tubular configuration, to form a single conduit. These pieces of tissue 101, 103 are merely representative of any two pieces of tissue which are to be joined or otherwise connected with one or more sutures.

Although the suturing device 10 can be used in an open procedure wherein the pieces of tissue are more accessible, the device 10 will be even more appreciated when the pieces of tissue are disposed within a cavity, such as an abdominal cavity 104, defined by a body wall, such as an abdominal wall 105. In such a method, the needle 18 of the suturing device 10 is initially inserted through the wall 105 typically with the suture line 14 and snare 61 retracted into the lumen 23. In some cases, the step of insertion may include the step of inserting the device through a trocar 107 which has been placed to provide access across the wall 105. Within the cavity 104 defined by the wall 105, a clamp 112 can be used to hold the pieces of tissue 101 and 103 in proximity. The clamp 112 will typically be inserted into the cavity 110 through a second trocar (not shown). This greatly facilitates insertion of the sharp point 33 of the needle 18 through the pieces of tissue 101, 103 which are to be joined.

Figure 4:
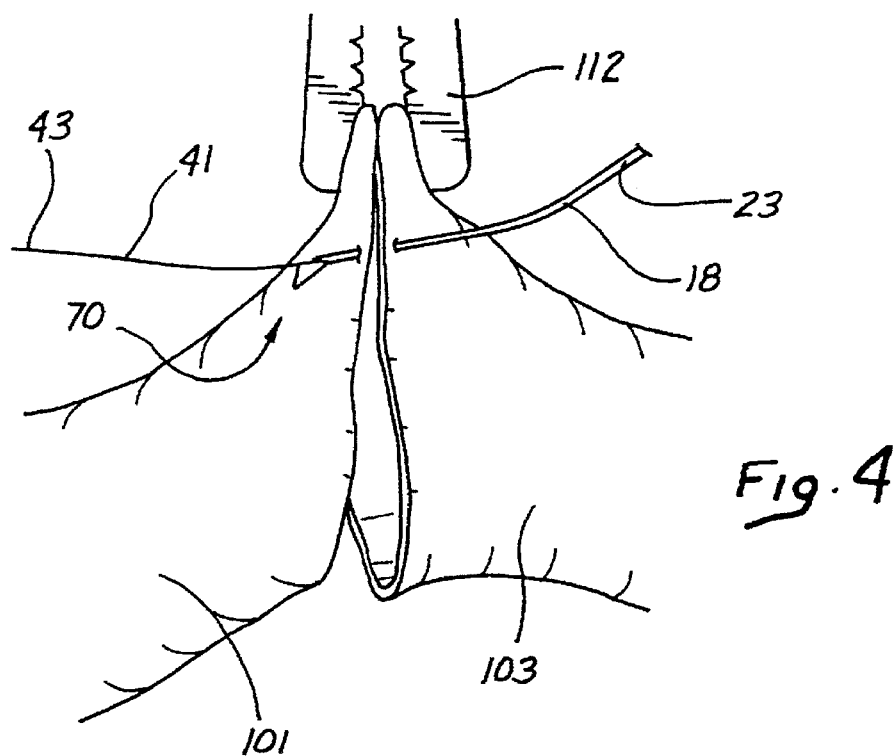

Up to this point, the suture line 41 and snare 61 will typically have been positioned within the lumen 23 of the needle 18 so as not to interfere with the sharp point 23. As illustrated in FIG. 4, once the needle 18 has been inserted through the pieces of tissue 101, 103, it is desirable to deploy the suture line 41. This is facilitated in a preferred method by initially deploying the hook 70 of the snare 61 as illustrated in FIG. 4. Once the hook 70 has been cleared from the lumen 23 by operation of the thumb wheel 83, the suture line 41 can be issued from this lumen 23 by operation of the thumb wheel 81.

Figure 5:
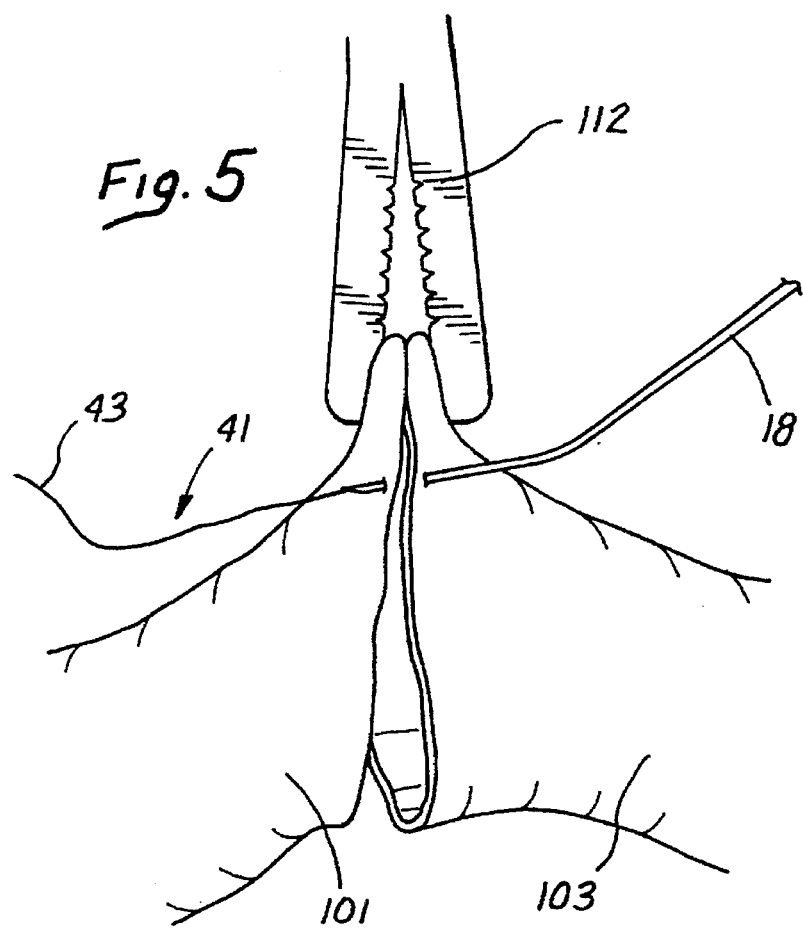

The next objective in a preferred method is to remove the needle 18 leaving the suture line 41 extending between the pieces of tissue 101 and 103. This step is facilitated by initially retracting at least the free end of the hook 70 into the lumen 23 as illustrated in FIG. 5. Then the needle 18 is free to be withdrawn from the pieces of tissue 101, 103. With the free end 43 of the suture line 41 extending through the tissue 101, and the proximal end 45 of the suture line 41 extending through the tissue 103, the hook 70 of the snare 61 can again be deployed as illustrated in FIG. 6.

It is the purpose of the hook 70 to engage the free end 43 of the suture line 41 and to capture it in a generally fixed relationship with the needle 18. This is accomplished with a preferred embodiment of the hook 70 best illustrated in the enlarged view of FIG. 7A. In this embodiment, the hook 70 is formed as an extension of the wire 67 and includes a first leg 121, a second leg 123 which is bent back on the first leg 121, and a third leg 125 which extends to a free end 127 of the hook 70. In the embodiment, an opening 130 is formed between the free end 127 and the leg 21 of the hook 70.

Three bends are formed in the wire 67 which are of particular interest to the hook 70. A first bend 132 is formed between the wire 67 and the first leg 121 of the hook 70. This bend 132 is formed in a single plane 137 (best illustrated in FIG. 7C) which includes both the wire 67 and the leg 121. A second bend 134 is formed between the first leg 121 and the second leg 123. This bend 134 is preferably formed with an inner radius which is smaller than the diameter of the suture line 141. A third bend 136 can be formed between the second leg 123 and the third leg 125. This bend 136 enables the second leg 123 to extend in close proximity to the first leg 121 while providing for an enlargement of the opening 130 between the third leg 125 and the first leg 121. For reasons discussed in greater detail below, it is preferable if the bends 134 and 136 are disposed in the same plane 137 as the bend 132.

When the hook 70 is disposed in a first position within the lumen 23 of the needle 18, the diameter of the lumen 23 dictates the size of the opening 130 as well as the proximity of the first and second legs 121, 123 as illustrated in FIG. 7B. When the hook 70 is deployed to its second position exterior of the lumen 23, the opening 130 is free to enlarge. This enlargement of the opening 130 is accompanied by a slight separation between the first and second legs 121, 123 respectively. It is in this second position that the hook 70 is best adapted to engage the free end 43 of the suture line 41. This is accomplished by manipulating the handle 21 of the suturing device 10 so that the opening 130 of the hook 70 moves over the free end 43 of the suture line 41. The suture line 41 can then be funneled between the third leg 125 and first leg 121, and into the narrow channel between the first leg 121 and second leg 123. This movement of the suture line 41 toward the second bend 134 is generally accomplished during retraction of the hook 70 back toward the needle 18.

Once the suture line 41 has been engaged, it is important to capture it so that the free end 43 does not slip through the hook 70. This capturing of the suture line 41 is accomplished during retraction of the hook 70 by operation of the thumb wheel 83. As the wire 67 of the snare 61 is withdrawn back into the lumen 23, the free end 127 of the third leg 125 engages the inner surface 25 of the needle 18. Further retraction of the snare 61 seeks to reduce the size of the opening 130 as the separation between the free end 127 and first leg 121 is increasingly dictated by the diameter of the lumen 23. As the opening 130 is reduced, the second leg 123 is moved into closer proximity with the first leg 121 and the suture line 41 is pinched or otherwise captured in the hook 70 as illustrated in FIG. 7B.

With the formation of the bends 132, 134 and 136 in the single plane 137, this movement of the hook between the first retracted position and the second deployed position will occur in the plane 137. If the bends 134 and 136 are formed in the same plane, the free end 127 will automatically extend through the lateral opening 34 upon retraction to engage the inner surface 25. This of course is desirable in order to ensure that the free end 127 of the hook 70 does not engage the needle 18 exteriorly of the lumen 23.

In this particular embodiment, the distal portions of the needle 18, which define the lateral opening 34, provide means for maintaining the hook 70 in its desired planar configuration as it moves between the first and second positions. The proximal most section of these distal portions, which is designated by the reference numeral 139 in FIG. 7c, tend to form a funnel which cooperates with the bend 132 to maintain the hook 70 in the plane 137. Any tendency of the hook 70 to move outside of the plane 137 is resisted by the walls of the tube 18 which form the opening 34 and by the tendency of the bend 132 to find the proximal most portion of the opening 34.

Figure 9:
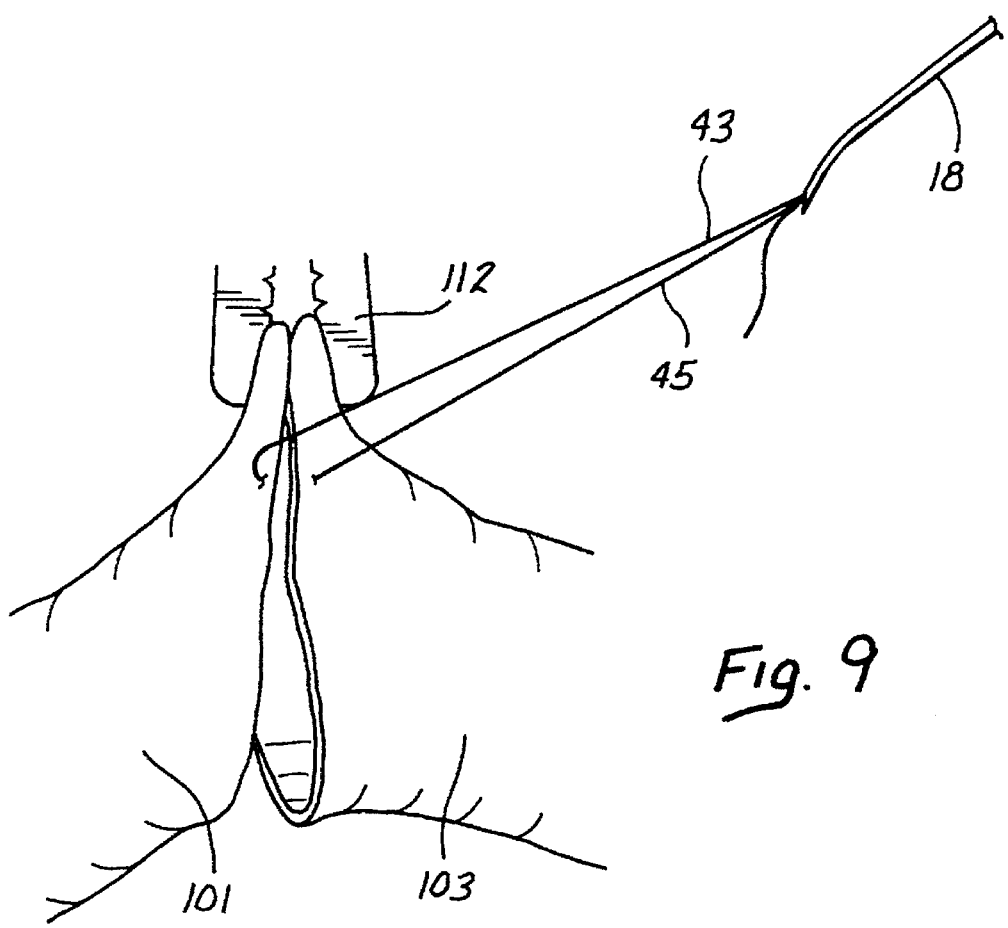

Once the free end 43 of the suture line 41 has been engaged and captured, and the hook 70 has been retracted back into the lumen 23, as illustrated in FIG. 8, the free end 43 has a generally fixed relationship with the needle 18. By comparison, the proximal end 45 of the suture line 41 is still free to move within the lumen 23. This enables the needle 18 to be removed from the suture site while the proximal end 45 of the suture line 41 issues from the needle 18 through the pieces of tissue 101, 103 and back to the fixed free end 43 and the needle 18 as illustrated in FIG. 9.

Figure 10:
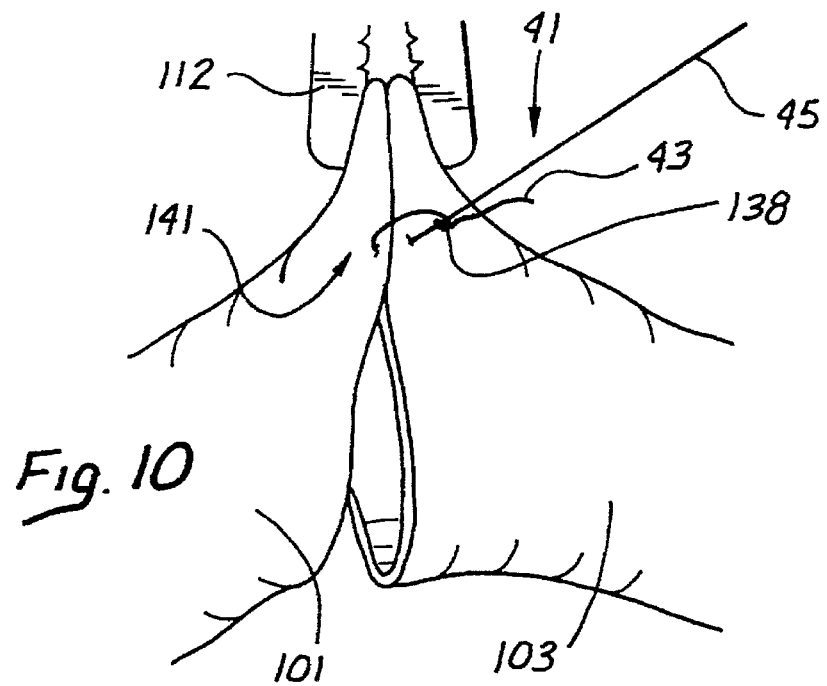

A knot 138 can be tied between the proximal end 45 and the distal end 43 of the suture line 41 either within the body cavity 110 or exteriorly of the body cavity 110. The knot 138 is typically formed as a slip knot so that it can be slid down the proximal end 45 of the suture line 41, as illustrated in FIG. 10, to form a suture 141 which binds the two pieces of tissue 101, 103 in a close, contacting relationship. After the suture 141 is formed, the proximal end 45 of the suture line 41 can be cut and the device 10 reinserted to form another suture.

From the foregoing description of preferred embodiments of the invention, it will be apparent that significant revisions can be made while still capturing the features and advantages of the concept. For example, it will be noted that the suturing device 10 can be used to form a running suture as well as the discreet sutures, such as the suture 141, previously described. It will also be apparent that the needle 18 can be formed with many different configuration to accommodate a particular body wall, cavity, tissue or suture configuration other embodiments of the device 10 will also be apparent for incorporating a suture line, such as the line 41, and a snare, such as the snare 61, within single or multiple lumens of a needle.

Many different configuration for the hook 70 will also be apparent for engaging and/or capturing the free end 43 of the suture line 41. Various embodiments for the mechanisms 50 and 72 will now be obvious for issuing the suture line 41 and either deploying or retracting the snare 61. Forming each of these mechanisms, 50, 72 as part of the handle 21 facilitates the single handed operation of the device 10. Although the thumb wheels 81 and 83 are pivotal on the common stationary shaft 85, this is certainly not a requirement of the concept.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A suturing device for capturing a suture line, comprising:

an elongate needle having an axis, a proximal end, a sharp distal tip, and a lumen carrying a suture line extending along the axis between the proximal end and the sharp distal tip;

a handle disposed at the proximal end of the needle;

a snare operable using the handle to engage and capture the suture line, the snare including a shaft mounted for axial movement between a retracted position and a deployed position, the shaft having a proximal end coupled to the handle and a distal end extending through the lumen of the needle, and a hook formed at the distal end of the shaft and movable from a closed state within the tip of the needle when the shaft is in the retracted position to an open state extending beyond and through the tip of the needle when the shall is in the deployed position;

a thumb wheel rotatable about an axis extending transverse to the axis of the needle; and means operable by the thumb wheel engaging the shaft of the snare for moving the hook to the open state to engage the suture line and for moving the hook to the closed state to capture the suture line.

2. The suturing device recited in claim 1 wherein the hook is formed from a wire and further comprises:

a first leg coupled to the shaft and extending at a first oblique angle to the shaft;

a second leg coupled to the first leg and bent back on the first leg; and a third leg coupled to the second leg and extending at a second oblique angle to the second leg away from the first leg to a free end of the hook.

3. The suturing device recited in claim 2 wherein the first leg, second leg and third leg are disposed on a common plane.

4. The suturing device recited in claim 3 wherein the shaft is disposed in the common plane with the first leg, second leg and third leg.

5. The suturing device recited in claim 3 wherein:

the free end of the hook in the open state is spaced a first distance from the first leg of the hook;

the free end of the hook in the closed state is spaced a second distance from the first leg; and the first distance is greater than the second distance.

6. The suturing device recited in claim 5 wherein the lumen of the needle is defined by an inner surface and the moving means includes means operable to move the free end of the hook in sliding engagement with the inner surface of the needle to move the hook between the open state and the closed state.

7. A suturing device for suturing tissue within a body cavity defined by a body wall, the device comprising:

an elongate needle having an axis, a proximal end, a sharp distal tip, and a lumen extending along the axis between the proximal end and the tip;

a handle coupled to the proximal end of the needle, the handle including an enclosure defining a chamber communicating with the lumen of the needle, the handle being sized and configured to be held in a single hand of a user;

a suture line having a first end and a second end, the first end extending through the lumen of the needle and the second end extending into the chamber of the enclosure;

first means included in the handle and operable by the single hand of the user for issuing the first end of the suture line through the tip of the needle;

a snare mounted for axial movement in the lumen of the needle, from a retracted position within the tip of the needle, to a deployed position extending beyond and through the tip of the needle;

and second means included in the handle and operable by the single hand of the user for advancing the snare from the retracted position to the deployed position to capture the first end of the suture and for withdrawing the snare and the captured first end of the suture line from the second position to the first position.

8. The suturing device recited in claim 7 wherein the first means comprises:

a thumb wheel rotatable around an axis extending transverse to the axis of the needle; and means operable by the thumb wheel for engaging the suture line and for moving the suture line axially of the lumen of the needle.

9. The suturing device recited in claim 8 wherein the thumb wheel is a first thumb wheel and the axis of the first thumb wheel is a first axis, the second mechanism comprising:

a second thumb wheel rotatable about a second axis transverse to the axis of the needle; and means operable by the second thumb wheel for engaging the snare and for moving the snare generally axially of the lumen of the needle.

10. A suturing device for capturing a suture line, comprising:

an elongate needle having an axis and a lumen extending along the axis between a proximal end and a sharp distal end;

a handle disposed at the proximal end of the needle;

a snare operable using the handle to engage and capture the suture line;

a shaft included in the snare and extending from the housing into the lumen of the needle;

a hook included in the snare and having an opened state and a closed state, wherein the hook is formed from a wire and includes
a first leg coupled to the shaft and extending at a first oblique angle to the shaft,
a second leg coupled to the first leg and bent back on the first leg, and
a third leg coupled to the second leg and extending at a second oblique angle to the second leg away from the first leg to a free end of the hook; and means included in the handle for moving the hook to the open state to engage the suture line and for moving the hook to the closed state to capture the suture line.

11. A method for suturing tissue within a body cavity defined by a body wall, comprising the steps of:

providing a device including an elongate needle having a proximal end and a distal end, and a handle disposed at the proximal end of the needle with a size adapted to be held in a single hand of a user;

positioning within the handle a suture line having a first end and a second end;

inserting the needle through the body wall by operation of the handle by the single hand of the user;

inserting the needle through the tissue in the body cavity by operation of the handle with the single hand of the user;

issuing the first end of the suture line through the needle by operation of the handle using the single hand of the user, to position the first end of the suture line on one side of the tissue and the second end of the suture line on the other side of the tissue;

capturing the first end of the suture line by operation of the handle using the single hand of the user; withdrawing the needle from the tissue following the issue step and prior to the capturing step; and tying a knot between the first end of the suture line and the second end of the suture line to form a suture around the tissue.

12. The method recited in claim 11 wherein the step of tying the knot further comprises the steps of:

withdrawing the device with the first end of the suture line and the second end of the suture line through the body wall;

tying the knot externally of the body cavity; and pushing the knot through the body wall to form the suture around the tissue within the body cavity.

13. The method recited in claim 12 wherein the capturing step includes the steps of:

providing a snare having a free end bent back on itself and defining a hook having an opening;

deploying the snare away from the tube by operation of the handle using the single hand of the user;

engaging the first end of the suture line with the snare;

retracting the snare and the first end of the suture line toward the tube by operation of the handle using the single hand of the user.

14. A method for capturing a suture line interiorly of a body cavity defined by a body wall, comprising the steps of:

providing a suturing device having an elongate tube with a lumen defined by an inner surface and extending between a proximal end and a distal end, a handle disposed at the proximal end of the tube, and a snare including a shaft extending from the handle into the lumen of the tube and a hook having a first leg coupled to the shaft and extending at a first oblique angle to the shaft, a second leg coupled to the second leg and bent back on the first leg, and a third leg coupled to the second leg and extending at a second oblique angle to the second leg away from the first leg to a free end of the hook, the hook having an open state to engage the suture line and a closed state wherein the third leg of the hook slidably engages the inner surface of the tube to capture the suture line;

inserting the tube through the body wall and into the body cavity, leaving the handle disposed exteriorly of the body cavity;

operating the handle to deploy the snare from the distal end of the tube;

operating the handle to move the shaft axially of the tube to deploy the snare from the lumen of the tube and move the hook to the opened state to engage the suture line; and operating the handle to retract the shaft axially into the tube and to move the hook to the closed state to capture the suture line.

15. A method for suturing tissue with a body cavity defined by a body wall, comprising the steps of:

providing a device including an elongate needle having a proximal end and a distal end, and a handle disposed at the proximal end of the needle with a size adapted to be held in a single hand of a user;

positioning within the handle a suture line having a first end and a second end;

inserting the needle through the body wall by operation of the handle by the single hand of the user;

inserting the needle through the tissue in the body cavity by operation of the handle with the single hand of the user;

issuing the first end of the suture line through the needle by operation of the handle using the single hand of the user, to position the first end of the suture line on one side of the tissue and the second end of the suture line on the other side of the tissue;

operating the handle to secure the first end of the suture line in generally fixed relationship with the needle; and tying a knot between the first end of the suture line and the second end of the suture line to form a suture around the tissue.

16. The method recited in claim 15, wherein the step of operating the handle to secure the first end of the suture line is carried out by the single hand of the user.

* * * * *